United States Patent
Archibald et al.

[11] Patent Number: 5,941,828
[45] Date of Patent: *Aug. 24, 1999

[54] HAND-HELD NON-INVASIVE BLOOD PRESSURE MEASUREMENT DEVICE

[75] Inventors: G. Kent Archibald, Vadnais Heights; Timothy G. Curran, Ramsey; Orland H. Danielson, Roseville; Marius O. Poliac, St. Paul; Roger C. Thede, Afton, all of Minn.

[73] Assignee: Medwave, Inc., Arden Hills, Minn.

[ * ] Notice: This patent is subject to a terminal disclaimer.

[21] Appl. No.: 08/912,139

[22] Filed: Aug. 15, 1997

Related U.S. Application Data

[63] Continuation-in-part of application No. 08/388,751, Feb. 16, 1995, Pat. No. 5,797,850, which is a continuation-in-part of application No. 08/227,506, Apr. 14, 1994, Pat. No. 5,450,852, which is a continuation-in-part of application No. 08/150,382, Nov. 9, 1993, abandoned.

[51] Int. Cl.$^6$ ........................................................ A61B 5/02
[52] U.S. Cl. ................................................................ 600/494
[58] Field of Search ............................ 600/485, 490–499

[56] References Cited

U.S. PATENT DOCUMENTS

| | | |
|---|---|---|
| 4,068,654 | 1/1978 | Paavola et al. .......................... 600/491 |
| 4,260,951 | 4/1981 | Lewyn . |
| 4,307,727 | 12/1981 | Haynes . |
| 4,461,266 | 7/1984 | Hood, Jr. et al. . |
| 4,482,266 | 11/1984 | Kaneko . |
| 4,664,126 | 5/1987 | Link . |
| 4,699,151 | 10/1987 | Link . |
| 4,712,563 | 12/1987 | Link . |
| 4,751,930 | 6/1988 | Terada et al. . |
| 4,799,491 | 1/1989 | Eckerle . |
| 4,830,017 | 5/1989 | Perry et al. . |
| 4,836,213 | 6/1989 | Wenzel et al. . |
| 4,928,702 | 5/1990 | Cousin . |
| 4,960,128 | 10/1990 | Gordon et al. . |
| 4,984,577 | 1/1991 | Frankenreiter . |
| 4,993,422 | 2/1991 | Hon et al. . |
| 5,025,792 | 6/1991 | Hon et al. . |
| 5,029,589 | 7/1991 | Kato . |
| 5,033,471 | 7/1991 | Yokoe et al. . |
| 5,163,438 | 11/1992 | Gordon et al. . |
| 5,170,795 | 12/1992 | Ramsey, III et al. . |
| 5,179,956 | 1/1993 | Harada et al. . |
| 5,218,967 | 6/1993 | Shinomiya et al. . |
| 5,238,000 | 8/1993 | Niwa . |
| 5,240,007 | 8/1993 | Pytel et al. . |
| 5,243,992 | 9/1993 | Eckerle et al. . |
| 5,247,944 | 9/1993 | Hirano et al. . |
| 5,253,648 | 10/1993 | Walloch . |
| 5,261,414 | 11/1993 | Aung et al. . |
| 5,263,484 | 11/1993 | Martin et al. . |
| 5,269,312 | 12/1993 | Kawamura et al. . |
| 5,271,405 | 12/1993 | Boyer et al. . |
| 5,284,150 | 2/1994 | Butterfield et al. . |
| 5,497,779 | 3/1996 | Takaya et al. . |

*Primary Examiner*—Samuel Gilbert
*Attorney, Agent, or Firm*—Kinney & Lange, P.A.

[57] ABSTRACT

A hand-held non-invasive blood pressure measurement device allows a varying pressure to be applied to an artery while pressure waveforms are sensed to produce pressure waveform data. Waveform parameters are derived from the sensed pressure waveform data. Blood pressure is then determined using the derived parameters. The user is guided or prompted to apply the varying pressure through audible and visual feedback.

84 Claims, 6 Drawing Sheets

HAND-HELD NON-INVASIVE BLOOD PRESSURE MEASUREMENT DEVICE

This is a continuation-in-part of application Ser. No. 08/388,751, filed Feb. 16, 1995, now issued as U.S. Pat. No. 5,797,850 and entitled "METHOD AND APPARATUS FOR CALCULATING BLOOD PRESSURE OF AN ARTERY", which is a continuation-in-part of application Ser. No. 08/227,506, filed Apr. 14, 1994, now issued as U.S. Pat. No. 5,450,852 and entitled "CONTINUOUS NON-INVASIVE BLOOD MONITORING SYSTEM", which is a continuation-in-part of application Ser. No. 08/150,382, filed Nov. 9, 1993 entitled "CONTINUOUS NON-INVASIVE BLOOD PRESSURE MONITORING SYSTEM", now abandoned.

BACKGROUND OF THE INVENTION

The present invention relates to systems for measuring arterial blood pressure. In particular, the invention relates to a method and apparatus for measuring arterial blood pressure in an non-invasive manner.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized or inflated to a predetermined amount. The cuff is then deflated slowly and the pressure within the cuff is continually monitored. As the cuff is deflated, the pressure within the cuff exhibits a pressure versus time waveform. The waveform can be separated into two components, a decaying component and an oscillating component. The decaying component represents the mean of the cuff pressure while the oscillating component represents the cardiac cycle. The oscillating component is in the form of an envelope starting at zero when the cuff is inflated to a level beyond the patient's systolic blood pressure and then increasing to a peak value where the mean pressure of the cuff is equal to the patient's mean blood pressure. Once the envelope increases to a peak value, the envelope then decays as the cuff pressure continues to decrease.

Systolic blood pressure, mean blood pressure and diastolic blood pressure values can be obtained from the data obtained by monitoring the pressure within the cuff while the cuff is slowly deflated. The mean blood pressure value is the pressure on the decaying mean of the cuff pressure that corresponds in time to the peak of the envelope. Systolic blood pressure is generally estimated as the pressure on the decaying mean of the cuff prior to the peak of the envelope that corresponds in time to where the amplitude of the envelope is equal to a ratio of the peak amplitude. Generally, systolic blood pressure is the pressure on the decaying mean of the cuff prior to the peak of the envelope where the amplitude of the envelope is 0.57 to 0.45 of the peak amplitude. Similarly, diastolic blood pressure is the pressure on the decaying mean of the cuff after the peak of the envelope that corresponds in time to where the amplitude of the envelope is equal to a ratio of the peak amplitude. Generally, diastolic blood pressure is conventionally estimated as the pressure on the decaying mean of the cuff after the peak where the amplitude of the envelope is equal to 0.82 to 0.74 of the peak amplitude.

The auscultatory method also involves inflation of a cuff placed around a cooperating artery of the patient. Upon inflation of the cuff, the cuff is permitted to deflate. Systolic pressure is indicated when Korotkoff sounds begin to occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. As a result, the oscillometric method does not produce blood pressure values that agree with the more direct and generally more accurate blood pressure values obtained from the A-line method. Furthermore, because the signal from the cuff is very low compared to the mean pressure of the cuff, a small amount of noise can cause a large change in results and result in inaccurate measured blood pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin of the patient. These tonometric systems measure a reference pressure directly from the wrist and correlate this with arterial pressure. However, because the ratio of pressure outside the artery to the pressure inside the artery, known as gain, must be known and constant, tonometric systems are not reliable. Furthermore, if a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff. With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

SUMMARY OF THE INVENTION

The present invention is an improved method and device for determining blood pressure of an artery having a pulse. As a varying pressure is manually applied to the artery, pressure waveforms are sensed to produce sensed pressure waveform data. The sensed pressure waveform data are then analyzed to derive waveform parameters. One or more blood pressure values are derived based upon the waveform parameters. The manual application of varying pressure is guided or prompted based upon the sensed pressure waveform data.

DETAILED DESCRIPTION OF THE PREFERRED EMBODIMENTS

Figure 1:
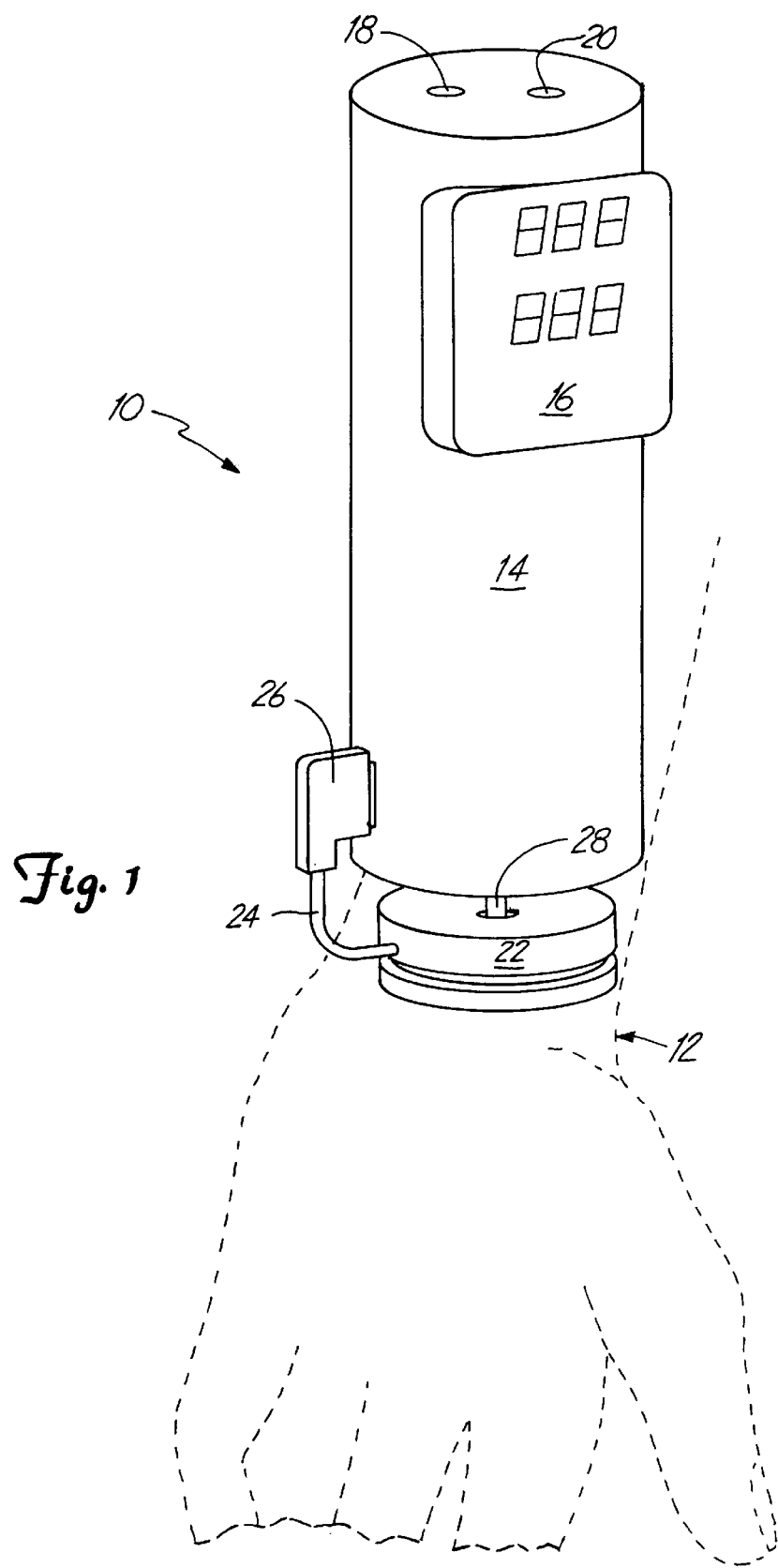
FIG. 1 is a perspective view of a blood pressure measuring device positioned over the wrist of a patient.

FIG. 1 illustrates a hand held blood pressure measurement device being used to measure and display blood pressure within an underlying artery within wrist 12 of a patient. With device 10, a small amount of force is manually applied to the radial artery at the projection of the styloid process bone. As the force is manually applied, cardiac pressure waveforms are recorded and the corresponding hold down pressure which is being manually applied is also recorded. Using the pressure shape of the cardiac pressure, waveform parameters are generated. These parameters, along with universal coefficients, are used to calculate pressure values which then can be displayed.

Blood pressure measurement device 10 includes main housing 14, display panel 16, on/off switch 18, display select switch 20, sensor interface assembly 22, connection cable 24, connection plug 26, and mounting stem 28.

Housing 14 contains all of the electrical components of measurement device 10. In the embodiment shown in FIG. 1, housing 14 is generally cylindrical in shape. Its diameter and length allow housing 14 to be easily held by the user (either medical personnel or the patient) during the measurement process. The hold down force is applied by applying force in an axial direction to wrist 12 which is transmitted from housing 14 through stem 28 to sensor interface assembly 22.

Display panel 16 is preferably a liquid crystal display (LCD). In a preferred embodiment, display panel 16 simultaneously displays a pair of values based upon blood pressure measurements. One pair of values represent systolic and diastolic pressure. Another pair of values represent pulse rate and mean blood pressure. Select switch 20 allows the user to select either pair of values to be displayed on display panel 16.

Power switch 18 is actuated to turn on power to the circuitry within housing 14. Timing circuitry within housing 14 automatically turns power off after a predetermined period of inactivity, or switch 18 may be manually toggled to the off state.

Sensor interface assembly 22 is pivotally mounted to a distal end of stem 28. As pressure is manually applied by moving housing 14 toward the artery, that force is transferred from housing 14 through stem 28 to sensor interface assembly 22. Sensor interface assembly 22 is generally similar in construction to the sensor interface assemblies described in the copending patent application entitled Method and Apparatus for Calculating Blood Pressure of an Artery, Ser. No. 08/388,751, filed Feb. 16, 1995, and assigned to Medwave, Inc., the assignee of the present application.

Cable 24 and connection plug 26 connect sensor interface assembly 22 to signal processing circuitry located within housing 14.

In operation, sensor interface assembly 22 is positioned over an artery such as the radial artery (as illustrated in FIG. 1). Alternatively, device 10 can be used in a number of other locations, such as on the temporal artery or the dorsalis pedis artery. The user then begins to apply force to the artery by applying axial force from housing 14 through stem 28 to sensor interface assembly 22. The force applied to the artery is swept in an increasing fashion so that pressure waveform data from a series of pulses are obtained with different amounts of force being applied. To achieve the desired pattern of variable force, user feedback is preferably provided with device 10. In a preferred embodiment, feedback is in the form of audible tones. As pressure is applied, device 10 emits a tone for each cardiac output waveform. Each tone is modulated and has a higher pitch sound as the amplitude of the cardiac waveform increases. By listening to the tone, the user knows at what rate to apply the pressure to the artery. At the point of maximum energy transfer between the artery and sensor interface assembly 22, the cardiac pressure waveform reaches a peak amplitude and, therefore, the highest frequency tone is produced. As the user continues to apply higher pressure to the artery, the amplitude of the cardiac pressure waveform decreases, and therefore the frequency of the tone decreases. By listening to the tone, the user can perform a variable pressure sweep to measure pressure using device 10.

Feedback to the user can be supplied in other ways as well. For example, an audible tone can be produced using a combination of frequency modulation and amplitude modulation. In other words, as the amplitude of the pressure waveform increases, both pitch (frequency) and amplitude (volume or loudness) of the tone will change.

In another embodiment, visual feedback is displayed to the user so that a correct pressure sweep is applied. The visual feedback can be through display panel 16, or through light emitting diodes positioned on housing 14, such as at the end of housing 14 which contains switches 18 and 20.

Figure 2:
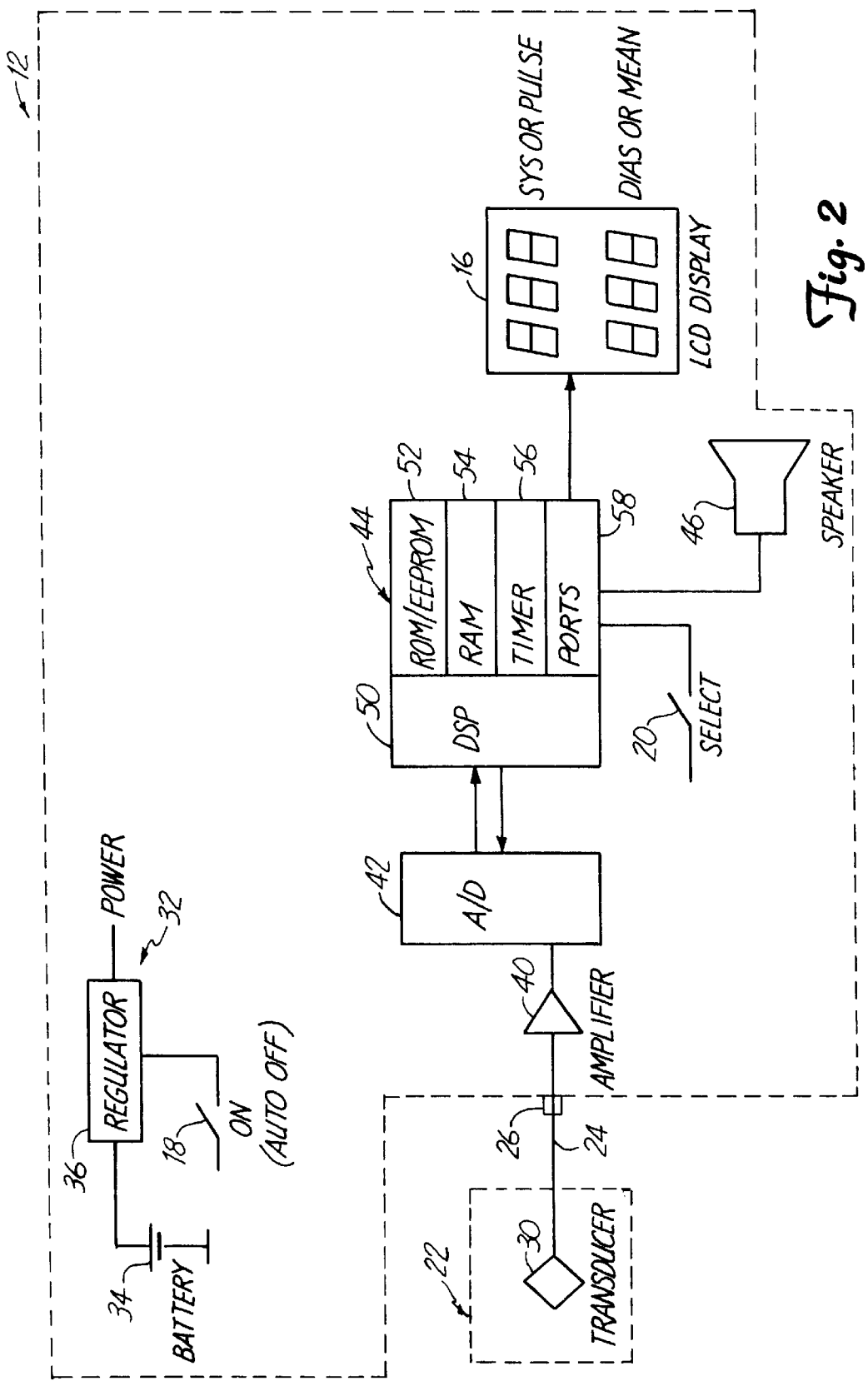
FIG. 2 is an electrical block diagram of the blood pressure measuring device of FIG. 1.

FIG. 2 is a electrical block diagram of device 10. Pressure transducer 30 within sensor interface assembly 22 is connected by cable 24 and connector 26 to circuitry within housing 12. Power supply circuit 32 includes battery 34, regulator 36, and switch 18. The output of regulator 36 is electrical power which is used to energize the remaining circuitry, which includes amplifier 40, analog to digital (A/D) converter 42, microprocessor 44, speaker 46, display panel 16 and select switch 20. Microprocessor 44 includes digital signal processing circuitry 50, read only memory (ROM) and electrically erasable programmable read only memory (EEPROM) 52, random access memory (RAM) 54, timer circuitry 56, and input/output ports 58.

Transducer 30 senses fluid pressure communicated to transducer 30 within sensor interface assembly 22 and supplies an electrical signal through cable 24 and connection plug 26. In a preferred embodiment, transducer 30 is a piezoresistive pressure transducer.

The output of transducer 30 is an analog electrical signal representative of sensed pressure. That signal is amplified by amplifier 40 and applied to an input of A/D converter 42. The analog signal to A/D convertor 42 is converted to digital data and supplied to the digital signal processing circuitry 50 of microprocessor 44.

Based upon the pressure data received, microprocessor 44 performs calculations to determine blood pressure values. Those calculations will be described in more detail with reference to FIGS. 4–6. As each pulse produces a cardiac waveform, microprocessor 44 determines a peak amplitude of the waveform. Microprocessor 44 drives speaker 46 to produce audible tones which vary as a function of the sensed waveform. The audible tones vary in frequency or amplitude (or both) to guide the user in applying a variable force to the artery.

When a measurement cycle has been completed, microprocessor 44 performs calculations to determine systolic pressure, diastolic pressure, mean blood pressure, and pulse rate. Depending upon the setting of select switch 20, microprocessor 44 provides display control signals to display 16. With one position of select switch 20, systolic and diastolic blood pressure are displayed. With the other position of select switch 20, pulse rate and mean blood pressure are displayed. Additional data may be displayed when select switch 20 is pressed.

Figure 3A:
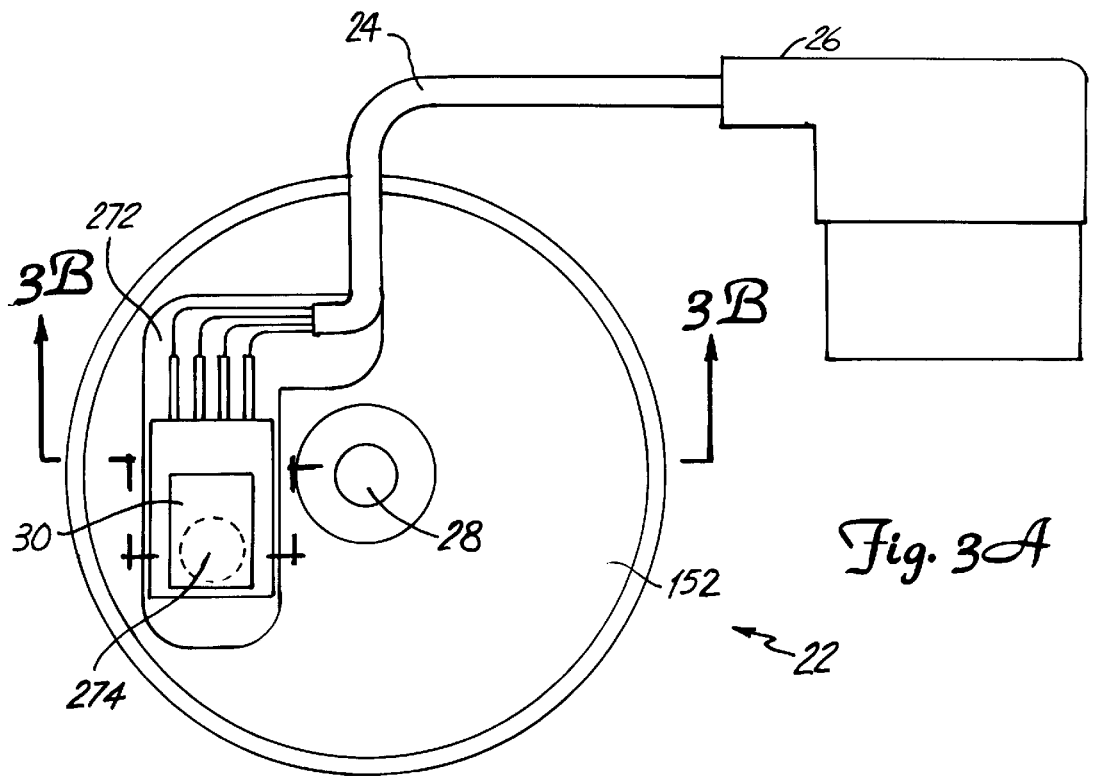
FIG. 3A is a top view of the sensor interface assembly.
Figure 3B:
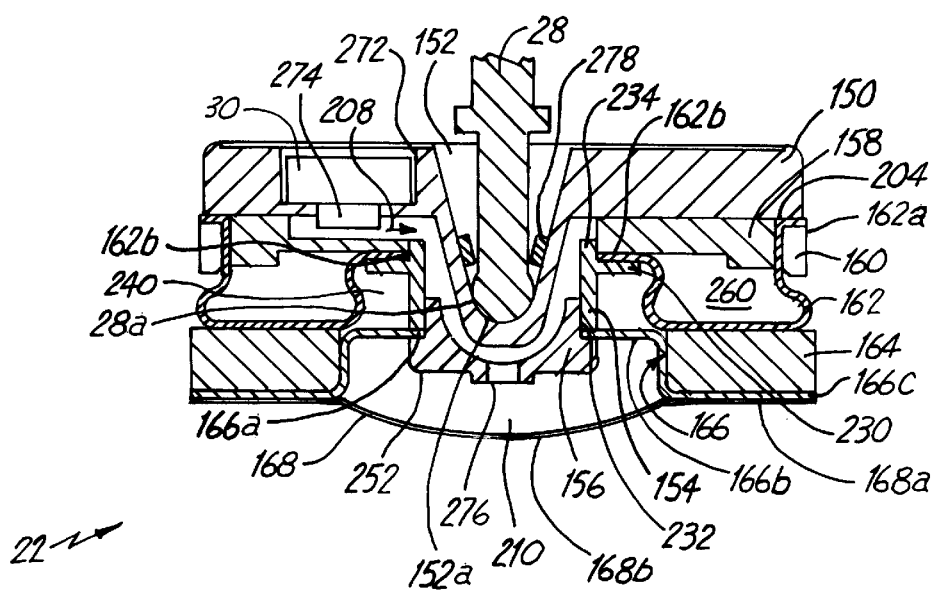
FIG. 3B is a cross-sectional view of the sensor interface assembly along section 3B—3B of FIG. 3A.

FIGS. 3A and 3B illustrate sensor interface assembly 22 (and the distal end of stem 28) in detail. Sensor interface assembly 22 includes top plate 150, upper cup 152, upper capture 154, diaphragm capture 156, inner mounting ring 158, outer mounting ring 160, side wall diaphragm 162, damping ring 164, inner diaphragm 166 and outer diaphragm 168.

Rings 158 and 160 and the upper outer end of side wall diaphragm 162 are mounted in shoulder 204.

Transducer 30 is placed in inset 272 in top plate 150. Transducer outlet 274 connects with fluid passage 208. Bore 276 also communicates with fluid passage 208 and fluid filled chamber 210. Detent 278 allows stem 28 to be snapped in place and removed as required. Multiconductor cable 24 connects transducer 30 to connector 26.

Fluid passage 208 is in fluid communication with sensor interface chamber 210. A fluid coupling medium fills chamber 210, passage 208, which connects to transducer 30. Ball 28 is pivotally mounted in socket 152a. Because socket 152a is adjacent to sensor interface chamber 210, sensor interface assembly 22 is pivotally coupled to stem 28 about a low pivot point. This permits sensor interface assembly 22 to be stably positioned above the underlying artery. In addition, the low pivot point enables the user to apply a more direct, uniform force on diaphragm 168. Thus, the hold down pressure manually applied by the user (through housing 14 and stem 28) is more uniformly applied to the anatomy above the underlying artery.

An outer surface or perimeter of upper capture 154 projects outwardly to form spar 230. Spar 230 partially supports side wall diaphragm 162, which is partially captured between ring 158 and spar 230. In the preferred embodiment, adhesive is used to bond the surfaces together. Other method such as ultrasonic welding or a press fit could be used. Expansion cavity 240 enables upper diaphragm 166 to initially change shape while only experiencing a small change in volume.

Diaphragm capture 156 is a elongated, annular ring including bore 276 and lower lip 252. Bore 276 extends through diaphragm capture 156 and defines a portion of fluid passage 208. Lip 252 projects outwardly from a lower end of diaphragm capture 156. Diaphragm capture 156 fits within bore 232 of upper capture 154 until an inner edge of diaphragm capture 156 is captured between lower lip 252 and the lower end of upper capture 154. Diaphragm capture 156 is preferably adhesively affixed to upper capture 154. Alternatively, diaphragm capture 156 may be press fit within upper capture 154.

Side wall diaphragm 162 and rings 158 and 160 define an annular deformable chamber 260 coupled to ring 164. Side wall diaphragm 162 is preferably formed from a generally circular sheet of flexible material, such as polyurethane, and is partially filled with fluid. Diaphragm 162 has a hole sized to fit around upper portion 234 of upper capture 154. Diaphragm 162 includes outer edge portion 162a and inner edge portion 162b. Outer edge portion 162a is trapped and held between outer ring 160 and top plate 150. Inner edge portion 162b is trapped and supported between ring 158 and spar 230 of upper capture 154. Diaphragm 162 is made from a flexible material and is bulged outward when chamber 260 is partially filled with fluid. Chamber 260 is compressible and expandable in the vertical direction so as to be able to conform to the anatomy of the patient surrounding the underlying artery. As a result, the distance between top plate 150 and the patient's anatomy can vary around the periphery of side wall diaphragm 162 according to the contour of the patient's anatomy. Furthermore, because fluid is permitted to flow through and around chamber 260, pressure is equalized around the patient's anatomy.

Damping ring 164 generally consists of an annular compressible ring and is preferably formed from a foam rubber or other pulse dampening material such as open celled foam or closed cell foam. Ring 164 is centered about and positioned between side wall diaphragm 162 and diaphragms 166 and 168. Damping ring 164 is isolated from the fluid coupling medium within chamber 210. Because ring 164 is formed from a compressible material, ring 164 absorbs and dampens forces in a direction parallel to the underlying artery which are exerted by the blood pressure pulses on sensor interface assembly 22 as the blood pressure pulse crosses sensor interface assembly 22. Because bottom ring 164 is isolated from the fluid coupling medium, the forces absorbed or received by ring 164 cannot be transmitted to the fluid coupling medium. Instead, these forces are transmitted across ring 164 and side wall diaphragm 162 to top plate 150. Because this path is distinct and separate from the fluid coupling medium, chamber 210 and the fluid coupling medium are isolated from these forces. In addition, ring 164 also presses tissue surrounding the artery to neutralize or offset forces exerted by the tissue.

Upper diaphragm 166 is an annular sheet of flexible material having an inner portion 166a, an intermediate portion 166b, an outer portion 166c and an inner diameter sized to fit around diaphragm capture 156. Inner portion 166a is trapped or captured between lip 252 of diaphragm capture 156 and the bottom rim of upper capture 154. Inner portion 166a is preferably adhesively affixed between lip 252 and upper capture 154.

Intermediate portion 166b lies between inner portion 166a and outer portion 166c. Intermediate portion 166b is adjacent to expansion cavity 240 and is isolated from ring 164 and chamber 260. Because intermediate portion 166b is positioned adjacent to expansion cavity 240, intermediate portion 166b is permitted to initially move upward into expansion cavity 240 as chamber 260, ring 164 and outer diaphragm 168 conform to the anatomy of the patient surrounding the underlying artery while chamber 260 experiences only a small change in volume. As ring 164 is pressed against the anatomy of the patient surrounding the artery to neutralize or offset forces exerted by the tissue, diaphragm 168 is also compressed. However, because intermediate portion 166b is permitted to roll into expansion cavity 240, chamber 210 does not experience a large volume decrease and a large corresponding pressure increase. Thus, sensor interface assembly 22 permits greater force to be applied to the anatomy of the patient through ring 164 to neutralize tissue surrounding the artery without causing a corresponding large change in pressure within chamber 210 as the height of the side wall changes. As a result, sensor interface assembly 22 achieves more consistent and accurate blood pressure measurements.

Outer diaphragm 168 is a generally circular sheet of flexible material capable of transmitting forces from an outer surface to fluid within chamber 210. Outer diaphragm 168 is coupled to inner diaphragm 166 and is configured for being positioned over the anatomy of the patient above the underlying artery. Outer diaphragm sheet 168 includes non-active portion or skirt 168a and active portion 168b. Skirt 168a constitutes the area of diaphragm 168 where inner diaphragm 166, namely outer portion 166c, is heat sealed or bonded to outer diaphragm 168. Skirt 168a and outer portion 166c are generally two heat sealed or bonded sheets of flexible material, forces parallel to the underlying artery are transmitted across skirt 168a and outer portion 166c and are dampened by the compressible material of ring 164.

Active portion 168b is constituted by the portion of outer diaphragm sheet 168 which is not bonded to inner diaphragm 166. Active portion 168b is positioned below and within the inner diameter of ring 164. Active portion 168b is the active area of sensor interface assembly 22 which receives and transmits pulse pressure to transducer 30. Active portion 168b of diaphragm 168, intermediate portion 166b of diaphragm 166 and diaphragm capture 156 define sensor interface chamber 210.

The coupling medium within chamber 210 may consist of any fluid (gas or liquid) capable of transmitting pressure from diaphragm 168 to transducer 30. The fluid coupling medium interfaces between active portion 168b of diaphragm 168 and transducer 30 to transmit blood pressure pulses to transducer 30. Because the fluid coupling medium is contained within sensor interface chamber 210, which is isolated from the side wall of sensor interface assembly 22, the fluid coupling medium does not transmit blood pressure pulses parallel to the underlying artery, forces from the tissue surrounding the underlying artery and other forces absorbed by the side wall to transducer 30. As a result, sensor interface assembly 22 more accurately measures and detects arterial blood pressure.

Sensor interface assembly 22 provides external measurements of blood pressure in an underlying artery. Because sensor interface assembly 22 senses blood pressure non-invasively, blood pressure is measured at a lower cost and without medical risks. Because sensor interface assembly 22 is relatively small compared to the larger cuffs used with oscillometric and auscultatory methods, sensor interface assembly 22 applies a hold down pressure to only a relatively small area above the underlying artery of the patient. Consequently, blood pressure measurements may be taken with less discomfort to the patient. Because sensor interface assembly 22 does not require inflation or deflation, faster, more frequent measurements may be taken.

Furthermore, sensor interface assembly 22 better conforms to the anatomy of the patient so as to be more comfortable to the patient and so as to achieve more consistent and accurate blood pressure measurements. Because chamber 260 is deformable and partially filled with fluid, chamber 260 better conforms to the anatomy of the patient and equalizes pressure applied to the patient's anatomy. Because ring 164 is compressible and because diaphragm 168 is flexible and is permitted to bow or deform inwardly, ring 164 and diaphragm 168 also better conform to the anatomy of the patient. At the same time, however, sensor interface assembly 22 does not experience a large sudden increase in pressure in sensor interface chamber 210 as ring 164 and diaphragm 168 are pressed against the anatomy of the patient. Chamber 260 and ring 164 apply force to the anatomy of the patient to neutralize the forces exerted by tissue surrounding the underlying artery. Because chamber 260 and ring 164 are both compressible, the height of the side wall decreases as side wall is pressed against the patient. Diaphragms 166 and 168 are also conformable. However, because intermediate portion 166b of inner diaphragm 166 is permitted to move upward into expansion cavity 240, sensor interface chamber 210 does not experience a large volume decrease and a corresponding large pressure increase. Thus, the side wall is able to apply a greater force to the anatomy of the patient without causing a corresponding large, error producing increase in pressure within sensor interface chamber 210 due to the change in height of the side wall and the change in shape of outer diaphragm 168.

At the same time, sensor interface assembly 22 permits accurate and consistent calculation of blood pressure. Because of the large sensing area through which blood pressure pulses may be transmitted to transducer 30, sensor interface assembly 22 is not as dependent upon accurate positioning of active portion 168b over the underlying artery. Thus, sensor interface assembly 22 is more tolerant to patient movement as measurements are being taken.

Moreover, sensor interface assembly 22 achieves a zero pressure gradient across the active face or portion 168b of the sensor, achieves a zero pressure gradient between the transducer and the underlying artery, attenuates or dampens pressure pulses that are parallel to the sensing surface of the sensor, and neutralizes forces of the tissue surrounding the underlying artery. Sensor interface assembly 22 contacts and applies force to the anatomy of the patient across skirt 168a and active portion 168b. However, the pressure within interface chamber 210 is substantially equal to the pressure applied across active portion 168b. The remaining force applied by sensor interface assembly 22 across skirt 168a which neutralizes or offsets forces exerted by the tissue surrounding the underlying artery is transferred through the side wall (ring 164 and chamber 260) to top plate 150. As a result, the geometry and construction of sensor interface assembly 22 provides the proper ratio of pressures between skirt 168a and active portion 168b to neutralize tissue surrounding the underlying artery and to accurately measure the blood pressure of the artery. In addition, because the fluid coupling medium within sensor interface chamber 210 is isolated from the side wall, pressure pulses parallel to the underlying artery, forces from tissue surrounding the underlying artery and other forces absorbed by the side wall are not transmitted through the fluid coupling medium to transducer 30. Consequently, sensor interface assembly 22 also achieves a zero pressure gradient between transducer 30 and the underlying artery.

Blood pressure measuring device 10 determines blood pressure values from the sensed waveform pressure amplitudes sensed by sensor interface assembly 22 and from other parameters derived from the pressure amplitudes using a stored set of coefficients. A pressure amplitude is determined at each sample point.

Device 10 calculates a systolic blood pressure value (S), a mean blood pressure value (M) and a diastolic blood pressure value(D) based upon the following formulas:

$$M = F_m(P_1^m, \ldots, P_n^m, C_1^m, \ldots, C_n^m)$$

$$S = F_s(P_1^s, \ldots, P_n^s, C_1^s, \ldots, C_n^s)$$

$$D = F_d(P_1^d, \ldots P_n^d, C_1^d, \ldots C_n^d)$$

wherein $F_m$, $F_s$, $F_d$ are linear or non-linear functions, $P_1^m$, $P_1^s$, $P_1^d$, ..., $P_n^m$, $P_m^s$, $P_n^d$ are parameters derived from waveform pressure amplitudes and $C_1^m$, $C_1^s$, $C_1^d$, ..., $C_n^m$, $C_n^s$, $C_h^d$ are coefficients obtained during training processes based upon clinical data.

In particular, device 10 calculates a systolic blood pressure value (S), a mean blood pressure value (M), a diastolic blood pressure value (D) based upon the following formulas:

$$M = C_1^m P_1^m + C_2^m P_2^m + \ldots + C_n^m P_n^m$$

$$S = C_1^s P_1^s + C_2^s P_2^s + \ldots + C_n^s P_n^s$$

$$D = C_1^d P_1^d + C_2^d P_2^d + \ldots + C_n^d P_n^d$$

wherein $P_1^m$, $P_1^s$, $P_1^d$ ... $P_n^m$, $P_n^s$, $P_n^d$ are parameters derived from waveform pressure amplitudes. Such parameters may be calculated from shape characteristics of the waveform or parameters calculated from functions such as curves based upon relationships between particular points of several waveforms. The parameters may be further based upon hold down pressure values and time periods between particular points on the waveforms. The value $C_1^m$, $C_1^s$, $C_1^d$ ... $C_n^m$, $C_n^s$, $C_n^d$ are coefficients obtained during training processes based upon clinical data.

In addition, the pulse rate (PR) may also be determined using the formula:

$$PR = \frac{PR_1 + PR_2 + PR_3 + PR_4}{4}$$

To determine pulse rate, four individual waveforms or beats are sensed and are time averaged to determine pulse rate. Preferably, the waveforms used to determine pulse rates include the waveform having largest maximum pressure amplitude, the two waveforms prior to the waveform having the largest maximum pressure and the waveform succeeding the waveform having the largest maximum pressure. Once the four waveforms are identified, the pulse rate of each waveform is determined. The sum of the pulse rate of the four waveforms is then divided by four to calculate pulse rate PR. The pulse rate (PR) for each waveform is based upon the following formula:

$$PR_N \text{ beats per minute } (N = 1, 2, 3, 4) = \frac{128 \text{ samples/sec}}{\text{No. samples/beat}_N} \times 60 \text{ sec/min}$$

Figure 4:
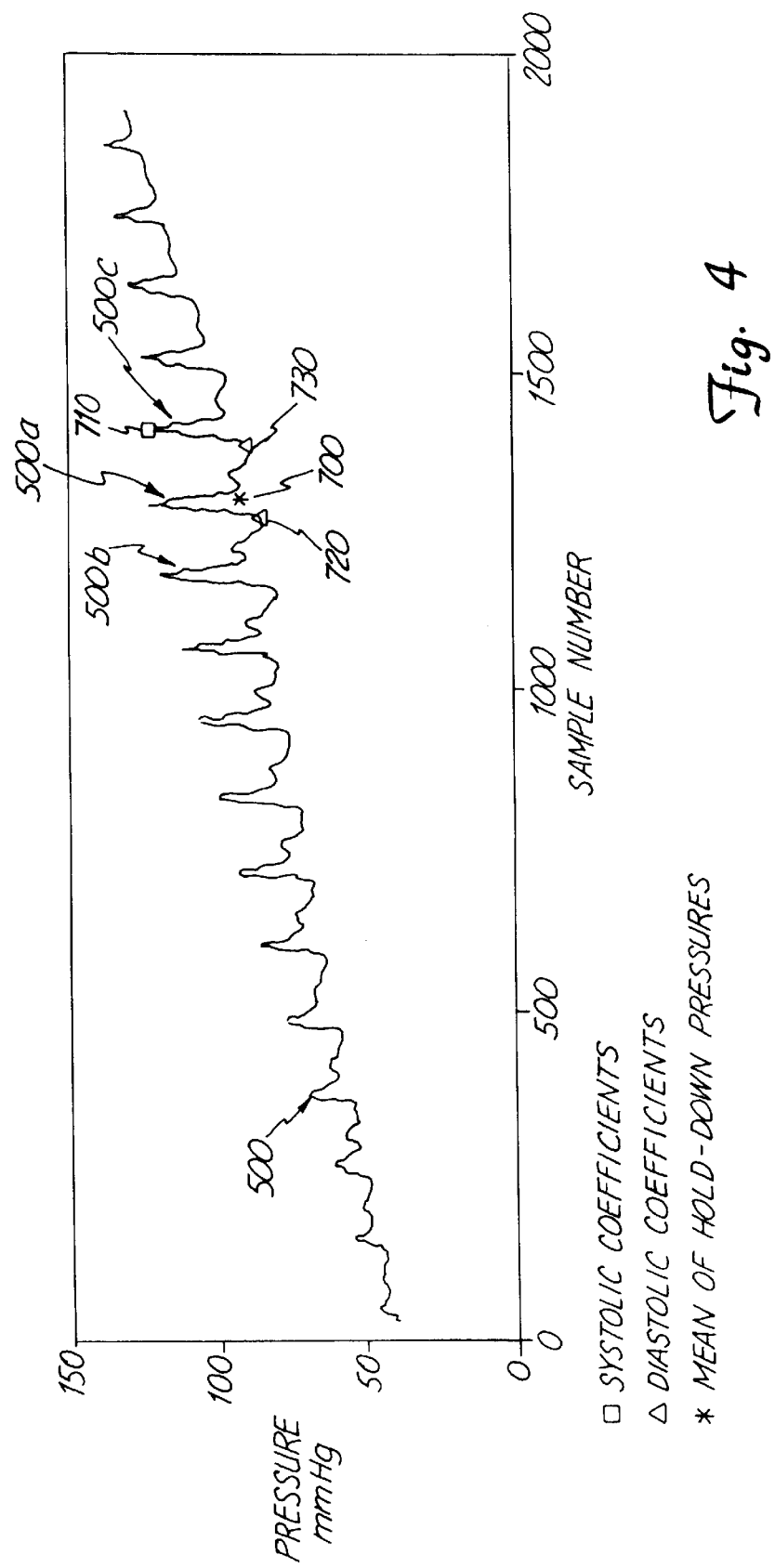
FIG. 4 is a graph illustrating blood pressure waveforms.
Figure 5:
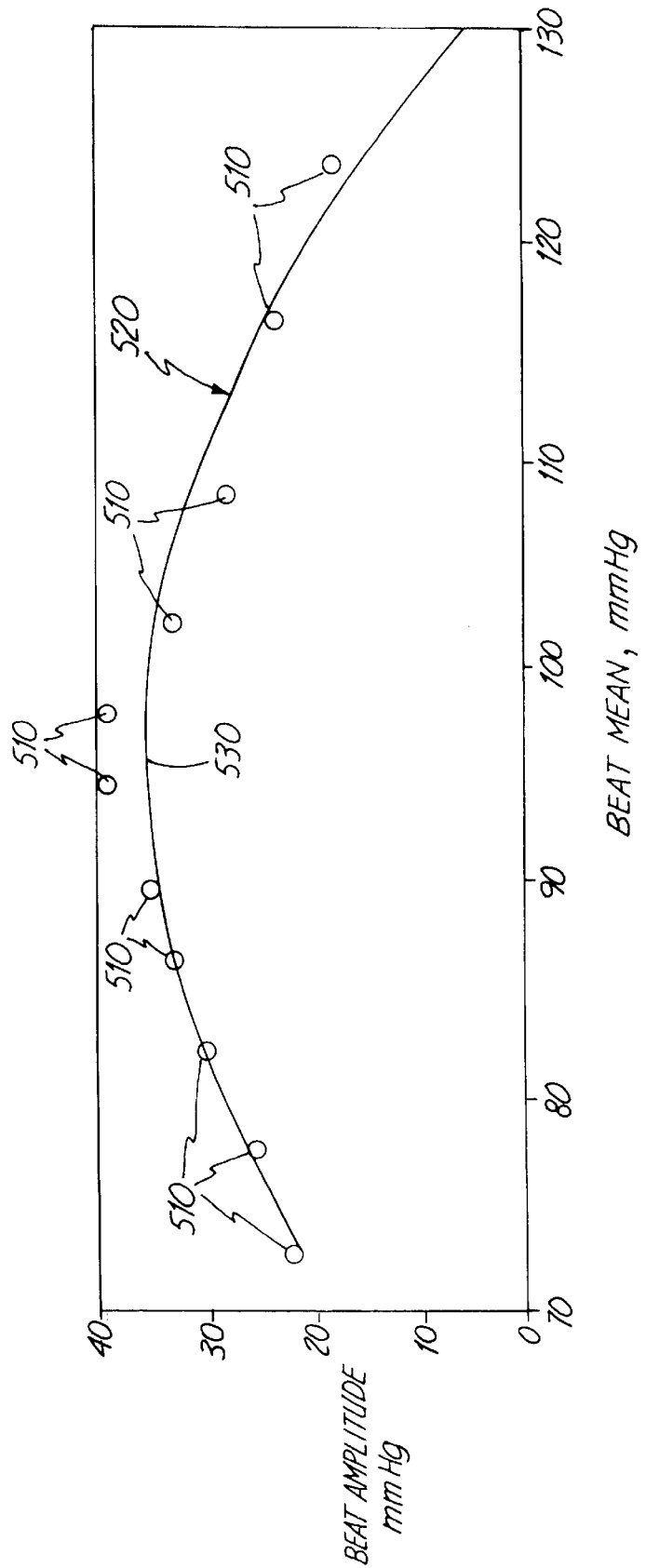
FIG. 5 is a graph illustrating a curve fit from points taken from the waveforms of FIG. 4.
Figure 6:
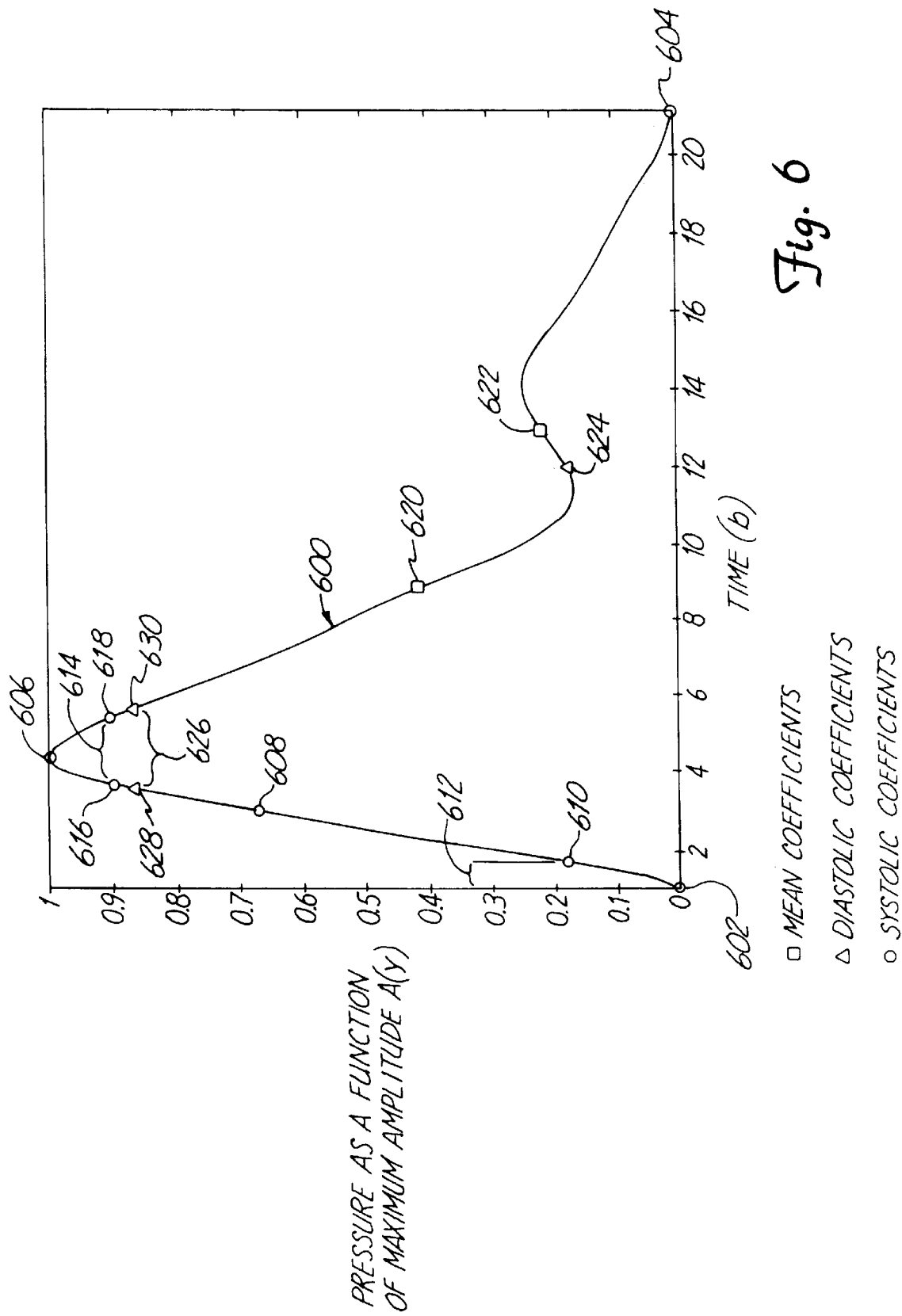
FIG. 6 is a graph illustrating a corrected and scaled waveform taken from the waveforms of FIG. 4.

FIGS. 4, 5 and 6 illustrate representative parameters which may be used to calculate blood pressure values. FIG. 4 illustrates a sample series of waveforms exhibited by the underlying artery as a varying pressure is applied over time. The vertical scale indicates pressure in mmHg while the horizontal scale indicates individual sample points at which the blood pressure values exerted by the pulse are measured over time. In the preferred embodiment, transducer 30 produces continuous electrical signals representing waveform pressures which are sampled 128 times per second.

In the preferred embodiment, the hold down pressure applied by to sensor interface assembly 22 (shown in FIGS. 1 and 3) is swept over a preselected range of increasing hold down pressures. Preferably, the sweep range of hold down pressures typically is begun at approximately 20 mmHg. The hold down pressure is then steadily increased (under the prompting or guidance from the audible or visual feedback) until two individual waveforms are sensed following the sensed waveform having the largest pressure amplitude. Preferably, each sweep range extends between an initial hold down pressure of about 20 mmHg and a final hold down pressure of approximately 150% of the mean hold down pressure of the waveform having the largest maximum pressure amplitude during the previous sweep.

Based upon sensed and sampled pressure waveform signals or data produced by transducer 30 during each sweep of hold down pressures, microprocessor 44 derives preselected parameters for calculating blood pressure values from the derived parameters and a stored set of coefficients. As indicated in FIG. 4, parameters may be derived directly from the absolute waveform pressures which vary as hold down pressure is varied over time. Such parameters may be derived from the shape of the waveforms including a particular waveform's slope, absolute pressure at a selected sample point, a rise time to a selected sample point on a waveform and the hold down pressures corresponding to a particular sample point on a waveform. As can be appreciated, any of a variety of parameters may be derived from the absolute waveform pressures shown in FIG. 4. Parameters may further be based upon particular points or functions of the sample points.

FIG. 5 illustrates an example of how values or parameters of multiple waveforms 500 shown in FIG. 4 may be used to derive additional parameters. FIG. 5 shows several data points 510. Each data point 510 represents a selected waveform taken from the sweep shown in FIG. 4. Curve 520 is derived by fitting points 510 to a preselected function or relationship. Parameters such as the peak 530 are then derived from curve 520. As can be appreciated, various other parameters such as slope may also be derived from curve 520. Parameters derived from curve 520 are ultimately based upon pressure waveforms 500 shown in FIG. 4 which are produced from sensed pressure waveform data or signals from transducer 30. However, because curve 520 is derived using a plurality of waveforms 500, parameters derived from curve 520 represent the overall relationship between the plurality of waveforms 500. In other words, parameters derived from curve 520 represent the way in which the plurality of waveforms 500 (shown in FIG. 4) are related to one another. Data points 510 represent corrected, relative waveform pressures. As can be appreciated, functions such as curves may also be derived using absolute waveform pressure values which are shown in FIG. 4.

A waveform is "corrected" by subtracting the hold down pressure from the absolute pressure of the waveform to produce relative waveform pressures (otherwise known as amplitudes). Correcting a waveform eliminates characteristics of the waveform which result from a continuously increasing hold down pressure being applied to the artery during each waveform or cardiac cycle.

In the application of device 10, the user may not apply a linear increase of pressure. Device 10 records the amplitude and hold down pressure. Even if these beats are recorded out of sequence, i.e. a beat with a corresponding higher hold down pressure is recorded before a beat with a low hold down pressure, microprocessor 44 can still generate a curve (such as curve 530 of FIG. 5) as long as there are several beats recorded over the pressure range. With this information recorded, microprocessor 44 can generate the required parameters and calculate pressure.

FIG. 6 further illustrates other parameters which may be derived from waveform pressure values as shown in FIG. 4. FIG. 6 illustrates waveform 600 selected from waveforms 500. Waveform 600 is preferably the waveform having the largest peak or maximum pressure amplitude. Alternatively, waveform 600 may be any of the waveforms 500 (shown in FIG. 4) such as waveforms immediately preceding or succeeding the waveform having the largest maximum pressure. As shown in FIG. 6, waveform 600 is corrected such that the beginning point 602 and an ending point 604 have the same absolute waveform pressure value. As further shown by FIG. 6, waveform 600 is horizontally and vertically scaled to eliminate gain from parameters derived from waveform 600. Preferably, waveform 600 is scaled from zero to twenty-one beginning at beginning point 602 and ending at ending point 604 of waveform 600 on the horizontal b axis. Preferably, waveform 600 is vertically scaled from zero to one beginning at its base and ending at its peak. Because waveform 600 is horizontally and vertically scaled, parameters may be derived from waveform 600 for calculating blood pressure values without the gain of the particular patient affecting the calculated blood pressure value. Gains are caused by the differences between the actual pressure exerted within the artery and the pressures sensed at the surface of the wrist or anatomy which is caused by varying characteristics of the intermediate tissue. Scaling waveform 600 eliminates any gains exhibited by individual patients. By using scaled values to locate corresponding points or waveform pressure amplitudes on waveform 600, points on waveform 600 uniformly correspond to the same points on waveforms exhibited by other patients.

As shown by FIG. 6, various parameters may be derived from scaled, corrected waveform 600. As shown by FIG. 6, such parameters include widths of waveform 600 at selected points along the vertical y axis, ratios of individual waveform pressure amplitudes at selected points along the horizontal b axis and the amplitude of the waveform, the rise time or time elapsed from the start of waveform 600 at point 602 to a selected point along the vertical y axis. In addition, several other parameters may also be derived from waveform 600, such as slope and other shape characteristics.

Once the parameters to be used in calculating blood pressure values are selected, coefficients corresponding to each parameter must be determined. Coefficients represent the relationship between a particular parameter set and the resulting blood pressure value to be determined from a particular parameter set. Coefficients are initially ascertained from clinical tests upon patients having known blood pressure values. Typically, the known blood pressure value is determined using the A-line method which is generally accurate, although difficult to set up, expensive and medically risky. As the blood pressure is determined using the A-line or other methods, sensor interface assembly 22 is positioned over the underlying artery of the patient. A varying pressure is applied to the artery of the patient having the known blood pressure value. As discussed above, transducer 30 produces sensed pressure waveform signals or data representing arterial pressure waveforms. Microprocessor 44 receives the produced sensed pressure waveform data and derives preselected parameters from the sensed pressure waveform data. Coefficients are then determined using the derived values of the selected parameters and the known blood pressure value. Each coefficient corresponding to each selected parameter is a function of the known blood pressure values and the derived parameters. Preferably, several patients are clinically tested to ascertain the coefficients. Once obtained, the coefficients are stored for use in non-invasively calculating blood pressure values of other patients without the necessity of using the more time consuming, expensive and risky A-line method and without using the generally more inaccurate conventional blood pressure measuring methods. Each particular coefficient is preferably ascertained so as to be applicable for calculating blood pressure values from the derived waveform parameters of all patients. Alternatively, individualized coefficients may be used to calculate blood pressure values from derived waveform parameters of particular patients falling within a particular age group or other specialized groups.

In addition to illustrating various methods by which parameters may be derived from waveform pressure data, FIGS. 4, 5 and 6 illustrate particular parameters for use in calculating a systolic, a mean and a diastolic blood pressure value of a particular patient during an individual hold down pressure sweep. According to the preferred method of the present invention, a sweeping, continuously varying hold down pressure is applied to the underlying artery. Preferably, the hold down pressure applied during each sweep begins at about 20 mmHg and ramps upward over time until at least two waveforms are detected by transducer 30 after the waveform having the largest maximum pressure is identified. Based upon the produced sensed pressure waveform data representing the waveforms as representatively shown by FIG. 4, microprocessor 44 calculates systolic, mean and diastolic blood pressure using a stored set of coefficients. Systolic blood pressure (S) is calculated using the formula:

$$S=C_1^s P_1^s+C_2^s P_2^s+C_3^s P_3^s+C_4^s P_4^s+C_5^s P_4^s+C_6^s P_6^s+C_7^s P_7^s+C_8^s P_8^s+C_9^s$$

Coefficients $C_1^s$–$C_9^s$ are stored coefficients ascertained according to the earlier described method of the present invention. $C_9^s$ is an offset value. Parameters $P_1^s$ and $P_2^s$ are derived from relative waveform pressure amplitudes corresponding to scaled values taken from a scaled and corrected beat as represented by waveform 600 in FIG. 6. Preferably, parameter $P_1^s$ is the ratio defined by the waveform pressure amplitude on waveform 600 which corresponds to scale value $b_1$ along the horizontal axis divided by the maximum waveform pressure amplitude or peak (point 606) of waveform 600. Parameter $P_2^s$ preferably is the ratio defined by the waveform pressure amplitude of point 608 on waveform 600 that corresponds to scale value $b_3$ along the horizontal b axis divided by the maximum waveform pressure amplitude or peak (point 606) of waveform 600.

Parameter $P_3^s$ is the rise time or the time elapsed from the start of the waveform to a particular point along waveform 600 corresponding to a particular vertical scale value. Preferably, parameter $P_3^s$ is the elapsed time from the start of waveform 600 to a point 610 on waveform 600 which has a vertical height of approximately 0.18 that of a maximum pressure amplitude or peak (point 606) of waveform 600. This rise time or elapsed time is represented as 612 in FIG. 6.

Parameter $P_4^s$ is the mean pressure of the uncorrected waveform 500a (shown in FIG. 4) having the highest peak or maximum pressure. Parameter $P_4^s$ is indicated on FIG. 4 by point 700. Parameter $P_5^s$ is the systolic point of the uncorrected pressure waveform immediately following the uncorrected pressure waveform having the largest maximum pressure. Parameter $P_5^s$ is represented by point 710 on FIG. 4.

Parameter $P_6^s$ is a parameter taken from a function such as a curve derived from values of a plurality of waveforms 500 (shown in FIG. 4). Preferably, parameter $P_6^s$ is the peak pressure of curve 520 shown in FIG. 5. The peak is represented by point 530. Curve 520 is preferably generated by fitting the relative waveform pressure amplitude of waveforms 500 (shown in FIG. 4) to the function or mathematical expression of:

$$\text{AMPLITUDE}=\exp(ax^2+bx+c),$$

wherein x=the mean pressure amplitude of each pressure waveform.

Parameter $P_7^s$ is a time value representing a width of waveform 600 (represented by segment 614 between points 616 and 618) which corresponds to a selected percentage of the maximum pressure amplitude or peak (point 606) of waveform 600. The time elapsed between points 616 and 618 is determined by counting the number of samples taken by monitor 26 which lie above points 616 and 618 on waveform 600. Preferably, parameter $P_7^s$ is the width of waveform 600 at a height of about 0.9 A, where A is the maximum waveform pressure amplitude of waveform 600 (point 606).

Parameter $P_8^s$ is the maximum slope of the uncorrected waveform 500c immediately following the waveform 500a having the largest maximum pressure or peak.

The mean blood pressure value (M) is calculated using the formula:

$$M=C_1^m P_1^m+C_2^m P_2^m+C_3^m P_3^m+C_4^m P_4^m+C_5^m$$

Coefficients $C_1^m$–$C_5^m$ are stored coefficients ascertained according to the earlier described method of the present invention. Coefficient $C_5^m$ is an offset. Parameters $P_1^m$ and $P_2^m$ are derived from relative waveform pressure amplitudes corresponding to scaled values taken from the scaled and corrected beat as represented by waveform 600 in FIG. 6. Preferably, parameter $P_1^m$ is the ratio defined by the waveform pressure (point 620) on waveform 600 which corresponds to the scale value $b_9$ along the horizontal axis divided by the maximum waveform pressure amplitude or peak (point 606) of waveform 600. Similarly, parameter $P_2^m$ is the ratio defined by the waveform pressure on waveform 600 which corresponds to scale value $b_{13}$ along the horizontal axis (point 622) divided by the maximum waveform pressure amplitude or peak (point 606) of waveform 600.

Parameter $P_3^m$ is identical to parameter $P_4^s$ used to calculate systolic blood pressure. Parameter $P_4^m$ is identical to parameter $P_6^s$ used to calculate systolic blood pressure.

Diastolic blood pressure values (D) are calculated using the formula:

$$D=C_1^d P_1^d+C_2^d P_2^d+C_3^d P_3^d+C_4^d P_4^d+C_5^d P_5^d+C_6^d P_6^d+C_7^d P_7^d+C_8^d$$

Coefficients $C_1^d$–$C_8^d$ are stored coefficients ascertained according to the earlier described method of the present invention. Coefficient $C_8^d$ is an offset value. Parameter $P_1^d$ is derived from relative waveform pressure corresponding to scaled values taken from a scaled and corrected beat as represented by waveform 600 in FIG. 6. Preferably, parameter $P_1^d$ is a ratio defined by the waveform pressure amplitude on waveform 600 which corresponds to scale value $b_{12}$ along the horizontal axis (point 624) divided by the maximum waveform pressure amplitude or peak (point 606) of waveform 600.

Parameter $P_2^d$ is identical to parameter $P_3^d$ used to calculate the systolic blood pressure. Preferably, parameter $P_3^d$ is the width of segment 626 between points 628 and 630. Preferably points 626 and 628 are points along waveform 600 that are located at a height of 0.875 A, where A is the maximum pressure amplitude (point 606) of waveform 600. The width or time of parameter $P_3^d$ is determined by counting the number of individual waveform pressure amplitude signals or samples generated by transducer 38 which lie above points 626 and 628 on waveform 600. If points 626 and 628 fall between individual waveform pressure amplitude signals or samples, interpolation is used to determine the time width of parameter $P_3^d$.

Parameter $P_4^d$ is identical to parameter $P_4^d$ used to calculate systolic blood pressure. Parameters $P_5^d$ and $P_6^d$ are calculated from absolute waveform pressures as illustrated in FIG. 4. Preferably, parameter $P_5^d$ is the diastolic pressure value of the uncorrected waveform having the largest maximum pressure value. This diastolic value is represented by point 720. Parameter $P_6^d$ is the diastolic pressure value of the uncorrected waveform (waveform 500c) immediately following the waveform (waveform 500a) having the largest maximum pressure amplitude or peak. Parameter $P_6^d$ is represented by point 730 on FIG. 4.

Parameter $P_7^d$ is derived from absolute waveform pressures illustrated in FIG. 4. To derive parameter $P_7^d$, the slopes along the portions of each individual waveform 500 are determined. Parameter $P_7^d$ is the hold down pressure applied to the underlying artery that corresponds to the point on the particular waveform having the maximum slope corrected amplitude. The slope corrected amplitude of a waveform is obtained by multiplying its amplitude with the maximum slope over all waveforms 500 and dividing the result with the slope corresponding to the individual waveform. As can be appreciated, various alternative parameters may also be used to calculate blood pressure values under the method of the present invention.

In preferred embodiments of the present invention, the waveform analysis described in Ser. No. 08/690,617 filed Jul. 31, 1996, now issued as U.S. Pat. No. 5,738,103 entitled "Segmented Estimation Method" and Ser. No. 08/690,627 filed Jul. 31, 1996, now issued as U.S. Pat. No. 5,720,292 entitled "Beat Onset Detector" are also used.

In conclusion, hand-held non-invasive blood pressure measurement device 10 offers a number of important advantages of prior art non-invasive blood measurement techniques. First, device 10 is small and easy to use in many different environments. For example, blood pressure often needs to be measured in a mobile setting such as when doctors and nurses are making rounds, at the scene of an accident, or while a patient is being transported. Prior art techniques which require the use of a cuff are not well suited for these environments.

Second, device 10 allows the pressure reading to be taken in a very short period of time. Prior art methods may take a minute or more to get a reading, while device 10 typically provides pressure readings within a few seconds.

Third, device 10 is easy to use. With audible or visual feedback, the user learns very quickly how to apply force in order to obtain blood pressure readings.

Fourth, the small size, quick readings, and easy use make device 10 particulary attractive for applications in which the user is measuring his own or her own blood pressure.

Although the present invention has been described with reference to preferred embodiments, workers skilled in the art will recognize that changes may be made in form and detail without departing from the spirit and scope of the invention. For example, although the determination of pressure values based upon waveform parameters has been described using linear equations and stored coefficients, other methods using non-linear equations, look-up tables, fuzzy logic and neural networks also can be used in accordance with the present invention. In still other embodiments, mechanical devices which release force at controlled rates (e.g. air cylinders) can be used to help control the sweep of pressure applied with device 10. In these embodiments, the release device will be referenced to the hand or part of body where the device is being used. The release rate provides for a sweep in applied pressure without the user having to control the force applied. The release rate may be user-adjustable in order to compensate for pulse rates.

In other embodiments, algorithms can be used that compensate for a non-linear hold down pressure sweep. This is accomplished by recording hold down pressure and pulse shape, so that the operation does not perform a linear sweep. A linear sweep can be constructed as long as there are several pulse shapes recorded over the range of the sweep, regardless of the order they are recorded.

What is claimed is:

1. A method for determining blood pressure of an artery having a pulse, the method comprising:

manually applying pressure to the artery;

sensing pressure data produced by the artery;

guiding the manually applying of pressure based upon the sensed pressure data;

deriving a plurality of parameters from the sensed pressure data; and determining a blood pressure value based upon the parameters.

2. The method of claim 1 wherein guiding the manually applying comprises producing a feedback signal which changes as a function of the sensed pressure data.

3. The method of claim 2 wherein the feedback signal is an audible signal.

4. The method of claim 3 wherein the audible signal changes in frequency as a function of pressure waveform amplitude derived from the sensed pressure data.

5. The method of claim 3 wherein the audible signal changes in volume as a function of pressure waveform amplitude derived from the sensed pressure data.

6. A method for determining blood pressure of an artery, the method comprising:

manually applying pressure to the artery so that the artery exhibits a plurality of pressure waveforms;

producing sensed pressure waveform data representing each of the plurality of pressure waveforms;

guiding the manually applying of pressure based upon the sensed pressure waveform data;

deriving a plurality of parameters from the sensed pressure waveform data; and determining a blood pressure value based upon the parameters.

7. The method of claim 6 wherein guiding the manually applying comprises producing a feedback signal which changes as a function of the sensed pressure data.

8. The method of claim 7 wherein the feedback signal is an audible signal.

9. The method of claim 8 wherein the audible signal changes in frequency as a function of pressure waveform amplitude derived from the sensed pressure data.

10. The method of claim 8 wherein the audible signal changes in volume as a function of pressure waveform amplitude derived from the sensed pressure data.

11. A non-invasive blood pressure measurement device, the measurement device comprising:

manually-operated pressure means for manually applying pressure to the artery so that the artery exhibits pressure data;

sensing means for sensing the pressure data;

signal producing means connected to the sensing means for producing output signals corresponding to the sensed pressure data;

means for guiding a user to manually apply pressure based upon the output signals; and processing means for receiving the output signals from the signal producing means, for deriving a plurality of parameters using sensed pressures and for determining a blood pressure value using the derived parameters.

12. The measurement device of claim 11, wherein the means for guiding produces a feedback signal which changes as a function of the sensed pressure data.

13. The measurement device of claim 12 wherein the feedback signal is an audible signal.

14. The measurement device of claim 13 wherein the audible signal changes in frequency as a function of pressure waveform amplitude derived from the sensed pressure data.

15. The measurement device of claim 13 wherein the audible signal changes in volume as a function of pressure waveform amplitude derived from the sensed pressure data.

16. The measurement device of claim 11 wherein the manually-operated pressure means comprises:

a housing shaped to be gripped by a user to apply force toward the artery.

17. The measurement device of claim 16 wherein the sensing means includes:

a transducer having a sensing surface;

a flexible diaphragm for being positioned over the underlying artery; and interface means between the flexible diaphragm and the sensing surface of the transducer for transmitting pressure pulses from the diaphragm to the transducer.

18. The measurement device of claim 17 wherein the flexible diaphragm is mounted on a sensor interface assembly which is pivotally connected to the housing.

19. A non-invasive blood pressure measurement system comprising:

means for manually applying pressure to an artery;

means for sensing pressure from the artery over time while the pressure is applied to the artery to generate pressure data;

means for guiding a user to manually apply the pressure; and means for deriving a pressure value based upon a waveform analysis of the pressure data.

20. The measurement device of claim 19, wherein the means for guiding produces a feedback signal which changes as a function of the sensed pressure data.

21. The measurement device of claim 19 wherein the feedback signal is an audible signal.

22. The measurement device of claim 19 wherein the audible signal changes in frequency as a function of pressure waveform amplitude denied from the sensed pressure data.

23. The measurement device of claim 19 wherein the audible signal changes in volume as a function of pressure waveform amplitude derived from the sensed pressure data.

24. The measurement device of claim 19 wherein the manually-operated pressure means comprises:

a housing shaped to be gripped by a user to apply force toward the artery.

25. The measurement device of claim 24 wherein the sensing means includes:

a transducer having a sensing surface;

a flexible diaphragm for being positioned over the underlying artery; and interface means between the flexible diaphragm and the sensing surface of the transducer for transmitting pressure pulses from the diaphragm to the transducer.

26. The measurement device of claim 25 wherein the flexible diaphragm is mounted on a sensor interface assembly which is pivotally attached to the housing.

27. A method of determining blood pressure, the method comprising:

applying pressure to an artery;

sensing pressure over time while the pressure is applied to the artery to generate pressure waveform data for pressure waveforms representing a plurality of beats;

guiding the applying of pressure based upon the pressure waveform data;

detecting onset of the beats from the waveform data;

extracting waveform parameters using a detected onset of one of the beats; and determining a blood pressure value based upon the waveform parameters.

28. The method of claim 27 wherein guiding the applying comprises producing a feedback signal which varies as a function of the sensed pressure data.

29. A method for determining blood pressure of an artery having a pulse, the method comprising:

applying pressure to the artery;

sensing pressure data produced by the artery;

guiding the applying of pressure based upon the sensed pressure data;

deriving a plurality of different parameters from the sensed pressure data; and determining a blood pressure value as a function of the plurality of different parameters.

30. The method of claim 29 wherein guiding the applying comprises producing a feedback signal which varies as a function of the sensed pressure data.

31. A method for determining blood pressure of an artery having a pulse, the method comprising:

sensing pressure data produced by the artery while manually applying pressure to the artery;

guiding the manually applying of pressure based upon the sensed pressure data;

deriving parameters from the sensed pressure data; and determining a blood pressure value based upon the parameters.

32. The method of claim 31 wherein guiding the applying comprises producing a feedback signal which varies as a function of the sensed pressure data.

33. The method of claim 32 wherein the feedback signal is an audible signal.

34. The method of claim 32 wherein the feedback signal is a visual signal.

35. A method for determining blood pressure of an artery having a pulse, the method comprising:

manually applying pressure to the artery;

sensing pressure data produced by the artery;

guiding the manually applying of pressure based upon the sensed pressure data;

deriving a plurality of parameters from the sensed pressure data; and determining a blood pressure value based upon the plurality of parameters and a stored set of coefficients.

36. The method of claim 35 including:

selecting a set of data from a plurality of beats including a maximum amplitude beat, wherein at least one parameter is derived from the selected set of data.

37. The method of claim 35 wherein deriving a plurality of parameters from the sensed pressure data includes deriving a relative amplitude value and at least one waveform shape parameter.

38. The method of claim 35 wherein deriving a plurality of parameters includes deriving parameters of a curve generated from the sensed pressure data.

39. The method of claim 35 wherein a first pressure is applied to the artery at a starting point of a waveform and wherein a second pressure is applied to the artery at an ending point of the waveform and wherein deriving a plurality of parameters includes adjusting the waveform so that the starting point and the ending point of the waveform have equal pressure amplitudes.

40. The method of claim 35 including:

scaling a pressure waveform to eliminate gain, wherein the parameters are derived from the scaled pressure waveform.

41. The method of claim 35 wherein deriving a plurality of parameters includes deriving at least one parameter selected from a group consisting of:

(a) rise time of a selected portion of a waveform, (b) slope of a portion of a waveform, (c) applied pressure corresponding to a starting point of a waveform, (d) applied pressure corresponding to an ending point of a waveform, (e) pressure of a waveform at a selected time, (f) a pressure corresponding to a selected point on a waveform, (g) a time value corresponding to a width of a selected portion of a waveform, (h) mean amplitude of a waveform, (i) an applied pressure corresponding to a selected point of a waveform, and (j) mean of a curve generated from data taken from a plurality of waveforms.

42. The method of claim 35 wherein deriving a plurality of parameters includes:

deriving at least one parameter other than pressure waveform amplitude from the sensed pressure data.

43. The method of claim 35 wherein the step of applying a varying pressure to the artery includes:

applying an increasing pressure to the artery.

44. The method of claim 35 including:

creating pressure waveform data of pressure waveforms representing a plurality of beats from the sensed pressure data;

detecting onset of the beats from the waveform data; and deriving at least one parameter using a detected onset of one of the beats.

45. A non-invasive blood pressure monitoring device, the monitoring device comprising:

manually-operated pressure means for applying a pressure to the artery so that the artery exhibits pressure data;

means for guiding a user in applying pressure to the artery with the manually operated pressure means based upon the pressure data;

sensing means for sensing the pressure data;

signal producing means connected to the sensing means for producing output signals corresponding to the sensed pressure data;

storing means for storing a set of coefficients; and processing means for receiving the output signals from the signal producing means, for deriving a plurality of parameters using sensed pressures and for determining a blood pressure value using the derived parameters and the stored set of coefficients.

46. The measurement device of claim 45, wherein the means for guiding produces a feedback signal which changes as a function of the sensed pressure data.

47. The measurement device of claim 45 wherein the feedback signal is an audible signal.

48. The measurement device of claim 45 wherein the audible signal changes in frequency as a function of pressure waveform amplitude derived from the sensed pressure data.

49. The measurement device of claim 45 wherein the audible signal changes in volume as a function of pressure waveform amplitude derived from the sensed pressure data.

50. The measurement device of claim 45 wherein the manually-operated pressure means comprises:

a housing shaped to be gripped by a user to apply force toward the artery.

51. The measurement device of claim 50 wherein the sensing means includes:

a transducer having a sensing surface;

a flexible diaphragm for being positioned over the underlying artery; and interface means between the flexible diaphragm and the sensing surface of the transducer for transmitting pressure pulses from the diaphragm to the transducer.

52. The measurement device of claim 51 wherein the flexible diaphragm is mounted on a sensor interface assembly which is pivotally attached to the housing.

53. A method for monitoring pressure waveform data produced by an artery, the method comprising:

manually applying pressure to the artery beginning with an initial pressure and ending with a final non-occluding pressure so that the artery exhibits a plurality of pressure waveforms; and sensing pressure waveform data produced by the artery representing each of the plurality of pressure waveforms, wherein the final non-occluding pressure applied to the artery is determined based upon the pressure waveform data sensed while pressure is applied to the artery.

54. The method of claim 53 and further comprising:

producing a feedback signal which changes as a function of the sensed pressure data.

55. The method of claim 54 wherein the feedback signal is an audible signal.

56. The method of claim 55 wherein the audible signal changes in frequency as a function of pressure waveform amplitude derived from the sensed pressure data.

57. The method of claim 55 wherein the audible signal changes in volume as a function of pressure waveform amplitude derived from the sensed pressure data.

58. The method of claim 53 and further comprising:

guiding the manually applying of the increasing pressure based upon the pressure waveform data.

59. A method for monitoring blood pressure parameters of an artery, the method comprising:

sensing pressure data produced by the artery over time representing a plurality of arterial pressure waveforms;

determining a maximum pressure amplitude for each of the plurality of arterial pressure waveforms from the sensed pressure data; and manually applying pressure to the artery while the pressure data is sensed based upon the maximum pressure amplitudes.

60. The method of claim 59 wherein the step of manually applying an increasing pressure to the artery includes:

manually applying the increasing pressure to the artery until at least one waveform has a maximum pressure amplitude less than a maximum pressure amplitude of a preceding waveform.

61. The method of claim 59 and further comprising:

prompting the manually applying of the increasing pressure based upon the pressure data sensed.

62. The method of claim 61 wherein prompting the manually applying comprises producing a feedback signal which changes as a function of the sensed pressure data.

63. The method of claim 62 wherein the feedback signal is an audible signal.

64. The method of claim 63 wherein the audible signal changes in frequency as a function of pressure waveform amplitude derived from the sensed pressure data.

65. The method of claim 63 wherein the audible signal changes in volume as a function of pressure waveform amplitude derived from the sensed pressure data.

66. A method for monitoring blood pressure data produced by an artery, the method comprising:

sensing pressure data produced by the artery over time representing a plurality of arterial pressure waveforms;

determining a maximum pressure amplitude for each of the plurality of arterial pressure waveforms from the sensed pressure data; and manually applying pressure to the artery until at least one waveform has a maximum pressure amplitude less than a maximum pressure amplitude of a preceding waveform.

67. The method of claim 66 and further comprising:

guiding the manually applying of increasing pressure based upon the sensed pressure data.

68. The method of claim 67 wherein guiding the manually applying comprises producing a feedback signal which changes as a function of the sensed pressure data.

69. The method of claim 68 wherein the feedback signal is an audible signal.

70. The method of claim 69 wherein the audible signal changes in frequency as a function of pressure waveform amplitude derived from the sensed pressure data.

71. The method of claim 69 wherein the audible signal changes in volume as a function of pressure waveform amplitude derived from the sensed pressure data.

72. A method for determining blood pressure of an artery, the method comprising:

positioning a sensor having a constant volume fluid filled sensing chamber over the artery;

manually applying force to the sensor to press the sensor towards the artery;

sensing pressure data produced by the artery by sensing pressure within the constant volume fluid filled chamber to generate pressure waveform data;

guiding the manually applying force based upon the pressure data;

deriving parameters from the pressure data; and determining a blood pressure value based upon the parameters.

73. The method of claim 72 wherein the step of manually applying force to the sensor includes:

manually applying an increasing force to the sensor.

74. The method of claim 73 wherein guiding the manually applying comprises producing a feedback signal which changes as a function of the sensed pressure data.

75. The method of claim 74 wherein the feedback signal is an audible signal.

76. The method of claim 75 wherein the audible signal changes in frequency as a function of pressure waveform amplitude derived from the sensed pressure data.

77. A non-invasive blood pressure measurement device comprising:

a sensor having a constant volume fluid filled sensing chamber configured for being positioned over an underlying artery;

manual force applying means for applying a force to the sensor to press the sensor against the underlying artery;

sensing means for sensing pressure within the constant volume fluid filled sensing chamber representing pressure data produced by the underlying artery;

prompting means for prompting a user to apply a force to the manual force applying means;

signal producing means connected to the sensing means for producing output signals corresponding to the sensed pressures within the constant volume fluid filled sensing chamber;

storing means for storing a set of coefficients; and processing means for receiving the output signals from the signal producing means, for deriving a plurality of parameters using the sensed pressures and for determining a blood pressure value using the derived parameters and the stored set of coefficients.

78. A non-invasive blood pressure measurement device comprising:

a sensor having a constant volume fluid filled sensing chamber configured for being positioned over an underlying artery;

means for manually applying force to the sensor to press the sensor against the underlying artery;

sensing means for sensing pressure within the constant volume fluid filled sensing chamber;

means for prompting a user to manually apply force to the sensor based upon the sensed pressure; and means for deriving a blood pressure value based upon a waveform analysis of the sensed pressure.

79. A method of non-invasive blood pressure measurement, the method comprising:

positioning a pressure sensor over an underlying artery;

prompting a user to apply force to press the sensor against the underlying artery;

deriving a blood pressure value based upon a waveform analysis of sensed pressure data.

80. The method of claim 79 wherein prompting the user is a function of the sensed pressure data.

81. A device for sensing blood pressure within an underlying artery of a patient, the device comprising:

a fluid filled sensing chamber having a diaphragm;

a transducer fluidly coupled to the fluidly filled sensing chamber, wherein the transducer senses fluid pressure within the chamber;

a flexible body conformable wall proximate the sensing chamber and isolated from the sensing chamber for applying force to the artery while preventing pressure in a direction generally parallel to the artery from being applied to the sensing chamber; and a housing connected to the wall for applying force to apply pressure to the artery.

82. A device for sensing blood pressure pulses within an underlying artery surrounded by tissue as the underlying artery is compressed, the sensor comprising:

a transducer;

a flexible diaphragm for placement above the underlying artery;

a fluid coupling medium between the transducer and the flexible diaphragm, wherein the fluid coupling medium transmits blood pressure pulse signals from the underlying artery to the transducer;

a flexible, variable height, body conforming sidewall isolated from the fluid coupling medium and positioned for engaging tissue proximate to the underlying artery; and means for manually applying force to the sidewall.

83. A device for external measurements of blood pressure in an underlying artery surrounded by tissue of a patient, the system comprising:

sensing means for sensing blood pressure pulses in the underlying artery;

means for manually applying a variable pressure to the sensing means; and means for calculating blood pressure based upon a pressure at maximum energy transfer and shape of the sensed pressure pulses within the underlying artery.

84. The device of claim 83 wherein the sensing means includes:

a transducer having a sensing surface;

a flexible diaphragm for being positioned over the underlying artery; and interface means between the flexible diaphragm and the sensing surface of the transducer for transmitting pressure pulses from the diaphragm to the transducer.

* * * * *